United States Patent
Yan et al.

(10) Patent No.: US 10,813,840 B2
(45) Date of Patent: Oct. 27, 2020

(54) INTELLIGENT CONTINUOUS MANUFACTURING METHOD VIA LIQUID COOLING OF DRIPPING PILLS

(71) Applicant: TASLY PHARMACEUTICAL GROUP CO., LTD., Tianjin (CN)

(72) Inventors: Kaijing Yan, Tianjin (CN); Xiaobing Sun, Tianjin (CN); Changsheng Rong, Tianjin (CN); Xuefei Cai, Tianjin (CN); Liang Wang, Tianjin (CN)

(73) Assignee: TASLY PHARMACEUTICAL GROUP CO., LTD., Tianjin (CN)

( * ) Notice: Subject to any disclaimer, the term of this patent is extended or adjusted under 35 U.S.C. 154(b) by 322 days.

(21) Appl. No.: 15/760,367

(22) PCT Filed: Sep. 14, 2016

(86) PCT No.: PCT/CN2016/099018
§ 371 (c)(1),
(2) Date: Mar. 15, 2018

(87) PCT Pub. No.: WO2017/045609
PCT Pub. Date: Mar. 23, 2017

(65) Prior Publication Data
US 2018/0256450 A1  Sep. 13, 2018

(30) Foreign Application Priority Data
Sep. 18, 2015  (CN) .......................... 2015 1 05985911

(51) Int. Cl.
*A61J 3/06* (2006.01)
*A61K 9/20* (2006.01)

(52) U.S. Cl.
CPC ............... *A61J 3/06* (2013.01); *A61K 9/2031* (2013.01); *A61K 9/2095* (2013.01)

(58) Field of Classification Search
CPC .................................. A61J 3/06; A61K 9/2031
See application file for complete search history.

(56) References Cited

U.S. PATENT DOCUMENTS

| | | | |
|---|---|---|---|
| 2002/0001461 A1* | 1/2002 | Bresolin | A01K 63/065 392/471 |
| 2009/0148536 A1* | 6/2009 | Guo | A61K 35/583 424/520 |
| 2009/0326025 A1* | 12/2009 | Lu | A61K 9/1623 514/381 |
| 2010/0034903 A1* | 2/2010 | Liu | A61K 36/77 424/725 |
| 2012/0315328 A1* | 12/2012 | Sun | A61K 9/1641 424/456 |
| 2013/0243644 A1* | 9/2013 | Guamis Lopez | A23L 3/18 422/1 |
| 2016/0030952 A1* | 2/2016 | Yarina | B04B 9/02 435/5 |
| 2016/0263041 A1* | 9/2016 | Wang | A61K 9/2095 |
| 2018/0263851 A1* | 9/2018 | Yan | A61J 3/06 |

FOREIGN PATENT DOCUMENTS

| | | | |
|---|---|---|---|
| CN | 1357412 A | * | 7/2002 |
| CN | 1660029 A | | 8/2005 |
| CN | 201042679 Y | | 4/2008 |
| CN | 101224198 A | | 7/2008 |
| CN | 101318162 A | | 12/2008 |
| CN | 101574305 A | | 11/2009 |
| CN | 101703487 A | | 5/2010 |
| CN | 101744722 A | | 6/2010 |
| CN | 101745472 A | | 6/2010 |

(Continued)

OTHER PUBLICATIONS

Zhao, H., 2014. Approaches to chemical-and activity-based standardization of traditional Chinese medicine (Doctoral dissertation, King's College London (University of London)). (Year: 2014).*
Zhang, L., Yan, B., Gong, X., Lawrence, X.Y. and Qu, H., 2013. Application of quality by design to the process development of botanical drug products: a case study. Aaps Pharmscitech, 14(1), pp. 277-286. (Year: 2013).*
Yang, D., 2010. Chinese medicine based on radix puerariae. (Year: 2010).*

(Continued)

*Primary Examiner* — Leith S Shafi
*Assistant Examiner* — Nicholas R Krasnow
(74) *Attorney, Agent, or Firm* — Baker & Hostetler LLP

(57) ABSTRACT

An intelligent continuous manufacturing method via liquid cooling of dripping pills comprises the following steps: (1) feeding: weighing and transferring multiple materials respectively; (2) material combining: performing staged heating on the materials transferred in step (1), and mixing the same to obtain a material mixture, wherein an RSD of an effective ingredient in the material mixture ≤5%; (3) homogenizing: pressurizing the material mixture obtained in step (2), and increasing the temperature, so as to obtain a homogenized material having the RSD of the effective ingredient in the material mixture ≤5%; (4) dripping: performing vibration dripping on the homogenized material obtained in step (3) to obtain dripping pills, delivering the dripping pills into a cooling liquid to be cooled and then transferred; and (5) de-oiling: removing the cooling liquid on surfaces of the dripping pills obtained in step (4) via tilting centrifugation. The manufacturing method not only shortens the manufacturing process, but also ensures the dripping pill product to be more stable and homogeneous. In addition, high-speed centrifugation is used to reasonably de-oil the dripping pills to prevent contamination of the dripping pills and improve the circulation utilization rate of the cooling liquid.

11 Claims, No Drawings

(56) References Cited

FOREIGN PATENT DOCUMENTS

| | | | |
|---|---|---|---|
| CN | 101279220 B | * | 6/2011 |
| CN | 102988420 A | | 3/2013 |
| CN | 203710386 U | | 7/2014 |
| CN | 104274319 A | | 1/2015 |
| CN | 104274322 A | | 1/2015 |
| CN | 104274518 A | | 1/2015 |
| CN | 104523623 A | | 4/2015 |
| RU | 2328300 C2 | | 7/2008 |
| TW | M479758 U | | 6/2014 |
| WO | WO 2015/003662 A1 | | 1/2015 |

OTHER PUBLICATIONS

International Patent Application No. PCT/CN2016/099018; Int'l Written Opinion and Search Report; dated Nov. 25, 2016; 9 pages.

* cited by examiner

INTELLIGENT CONTINUOUS MANUFACTURING METHOD VIA LIQUID COOLING OF DRIPPING PILLS

CROSS-REFERENCE TO RELATED APPLICATIONS

This application is the National Stage of International Application No. PCT/CN2016/099018, filed Sep. 14, 2016, which claims the benefit of Chinese application number 2015105985911, filed Sep. 18, 2015 the disclosures of which are incorporated herein by reference in their entireties.

TECHNICAL FIELD

The present invention relates to the technical field of drug manufacturing, especially to the manufacturing equipment for drugs of dripping pills. More specifically, it relates to an intelligent continuous manufacturing method via liquid cooling of dripping pills.

BACKGROUND OF THE INVENTION

The dripping pill is a traditional dosage form in traditional Chinese medicine preparations, and is universally recognized because of its many advantages like short production cycle, rapid effect, high drug stability and convenience in carrying and storage.

The prior production method of dripping pills is basically natural dripping in combination with liquid cooling or the pressurized dripping method improved from the natural dripping method and in combination with liquid cooling. The method of the prior art has the following defects: 1. the overall production process takes a long time, and ingredient volatilization caused by some volatile ingredients contained in materials makes it hard to ensure that dripping pills are consistent and stable in product quality; 2. the absence of a feeding system leads to poor uniformity of effective ingredients in dripping pills; 3. moreover, the adoption of liquid cooling requires liquid-solid separation for dripping pills and cooling liquid, the separation of the two is very hard to be operated, therefore it is inevitable that cooling liquid may remain on dripping pills and thus contaminate them. 4. normally, when adjustments are required for the production yield, traditional dripping equipment can only achieve that by changing its dripper and pressure, leading to a low dripping frequency, moreover, as a large heat exchange surface area is required for paraffin cooling liquid, the cycling efficiency is low, and the power consumption is high, leading to large volume of the equipment, dead corners hard to be cleaned are easy to be existed, and risks of cross contamination are high.

The development trend and research direction for the improvement on the production method of dripping pills at present lies in how to improve the prior production method of dripping pills, which includes guaranteeing the stability in the manufacturing process of dripping pills, effectively improving the forming quality of dripping pills and increasing production speed, and expanding the size range of dripping pills that can be dripped while reducing energy consumption and usage amount of cooling liquid as well as avoiding contamination on dripping pills.

SUMMARY OF THE INVENTION

Aimed at the above-mentioned deficiencies and problems existing in the prior art, the object of the present invention is to provide an intelligent continuous manufacturing method via liquid cooling of dripping pills, which not only shortens the time required by the overall manufacturing process, ensures the dripping pills to be more stable and homogeneous, but also prevents contamination of the dripping pills as well as improves the circulation utilization rate of cooling liquid by employing high-speed centrifugation to de-oil dripping pills in a reasonable manner.

To achieve the above object, the present invention employs the following specific technical solution:

An intelligent continuous manufacturing method via liquid cooling of dripping pills, wherein the method comprises the following steps:

1) feeding: weighing and transferring multiple materials respectively;

2) material combining performing staged heating on the materials transferred in step 1), and mixing the same to obtain a material mixture, wherein RSD of the effective ingredients in the material mixture is less than or equal to 5%;

3) homogenizing: pressurizing the material mixture obtained in step 2), and increasing the temperature so as to obtain a homogenized material with RSD of the effective ingredients less than or equal to 5%;

4) dripping: performing vibration dripping on the homogenized material obtained in step 3) to obtain dripping pills, and delivering the dripping pills into a cooling liquid to be cooled and then transferred;

5) de-oiling: removing the cooling liquid on surfaces of the dripping pills transferred in step 4) via tilting centrifugation.

Further, the removing performed via tilting centrifugation in step 5) has a centrifugal acceleration of 500-2000 G and a tilting lead angle of 40-90 degrees, with the removing time for each dripping pill not exceeding 30 seconds; the direction of the central rotation axis to which the centrifugal acceleration is directed is horizontal. That is, a horizontal centrifugal structure is employed.

Preferably, the removing performed via tilting centrifugation in step 5) has a centrifugal acceleration of 600-1800 G and a tilting lead angle of 50-80 degrees, with the removing time for each dripping pill not exceeding 20 seconds.

Further, the weighing in step 1) is the weightless weighing (i.e. the acceleration of materials approaches zero when being weighed), wherein the weight ratio of drugs to excipients is 1:5-5:1. Further, the time taken by the staged heating and mixing of the materials in step 2) is not more than 60 seconds, preferably not more than 30 seconds. The above staged heating and mixing comprises: heating solid ones of the materials to 50±10° C.; then, mixing them with liquid ones of the materials to obtain a material mixture; continuing to heat to 55±10° C.; thereafter, three steps of secondary mixing, de-gassing and delivering are performed successively, with a temperature increase of 0-10° C. in each step. When the process of material combining is finished, the temperature is below 80° C., which is preferred to be 60-70° C.

Further, for pressurizing the material mixture and increasing the temperature in step 3), the applied pressure is 50-200 MPa, preferably 70-160 MPa, and the temperature is increased by 10-20° C. After finishing pressurizing and increasing the temperature in the step of homogenizing, the temperature can reach to 80-100° C., preferably 90-95° C. The outlet pressure of a homogenizing device is 0.005-0.5 MPa, preferably 0.1-2 MPa.

Further, the vibration frequency of the vibration dripping in step 4) is 10-500 Hz, preferably 30-200 Hz. By adjusting the pressure at the outlet of the homogenizing device, the diameter of the dripped dripping pills can be controlled to be 1-10 mm, preferably 1-5 mm.

Further, the cooling liquid in step 4) has a temperature gradient, wherein the temperature gradient has a range of −15-60° C., preferably 0-50° C., dripping pills pass through the cooling liquid from high temperatures to low temperatures. The initial temperature of the cooling liquid at the bottom of a feed barrel is −15-25° C. With the liquid level of the cooling liquid rising in the feed barrel, the temperature is also increased gradually from bottom to top to form a temperature gradient having a range of −15-60° C.

Further, the cooling liquid in step 4) comprises paraffin, methylsilicone oil, kerosene and so on, and is preferred to be liquid paraffin.

Further, the time taken by the vibration dripping and cooling in step 4) is not more than 60 seconds, preferably not more than 30 seconds.

Further, the multiple materials comprise a dmg and an excipient. The dmg is selected from one of extracts of Radix Bupleuri, Salvia Miltiorrhiza, Qishen, Agastache rugosus and Herba andrographitis or the extract of Fufang Danshen, preferably the extract of Fufang Danshen; it can also be selected from an effective ingredient of compound preparations such as commercially available Qishen Yiqi Dripping Pills, Huoxiang Zhengqi Dripping Pills or Fufang Danshen Dripping Pills, preferably an effective ingredient of Fufang Danshen Dripping Pills.

The excipient is selected from one or more of polyethylene glycol, sorbitol, xylitol, lactitol, maltose, starch, methylcellulose, carboxymethylcellulose, hydroxypropyl methylcellulose, Arabic gum, trehalose, dextrin, cyclodextrin, agar and lactose. It is selected preferably from polyethylene glycol.

The present invention has the following beneficial effects:

As can be learned from the description of the above technical solution, various steps of the present method are linked closely, and constitute continuous operations. This method is featured by flexible batches, consistent and stable quality in products between batches, high yield and little material residues, with the manufacturing time for the whole dripping pill being less than 3 minutes; it overcomes the defect present in the prior art that ingredient volatilization and quality instability caused by some volatile ingredients contained in materials. Dripping pills manufactured via the method of the present invention are featured by good quality consistency, and as the weightless weighing is employed, the accuracy of dose may be up to 0.5‰.

Besides, the size of dripping pills can be adjusted by controlling the pressure of the outlet for the homogenized materials, without the need to change the dripper used during dripping, thus facilitating the adjustment on product specifications.

EMBODIMENTS OF THE INVENTION

The foregoing features and advantages of the present invention will be apparent from the following detailed description of the preferred embodiments.

Embodiment 1 Manufacture of Fufang Danshen Dripping Pills 600 g of extracts of Salvia Miltiorrhiza and Panax notoginseng, 5 g of borneol and 2000 g of PEG-6000 excipients were taken, after precise weighing was performed respectively, borneol and PEG-6000 were firstly heated for material combining, with the temperature being increased to 55° C., then, they were further mixed with the extracts of Salvia Miltiorrhiza and Panax notoginseng, and continuously heated to 60° C., the final temperature of the material mixture reaches to 65° C. after mixing, de-gassing, delivering and other steps were performed continuously, the time taken by the above material combining process was not more than 60 seconds. The homogenizing pressure was adjusted to be 2000 MPa to make the material mixture further be dispersed uniformly so as to reach to nano-scale dispersion, and the material temperature was further increased, the temperature of the material mixture at the outlet of the homogenizing device was 80° C., and the outlet pressure of the homogenizing device was 2 MPa. The material mixture was subjected to vibration dripping via a dripper, and the vibration frequency was adjusted to be 50 Hz, the material was dripped into a feed barrel containing liquid paraffin, the dripper was 300 mm away from the top liquid level of the liquid paraffin, the height of the feed barrel was 5 m, the diameter of the feed barrel was 100 mm, and the initial temperature of the inlet for the liquid paraffin was −10° C., a temperature gradient was formed from bottom to top in the feed barrel, which had a gradient range of −10-50° C., after the material was dripped into the liquid paraffin, under the action of temperature, the dripped material was cooled into solid dripping pills via sufficient cooling, and the dripped dripping pills had a diameter of 5 mm, wherein the time taken by the above dripping process was not more than 60 seconds. The de-oiling step was performed after the formed dripping pills were pre-filtrated together with the liquid paraffin via a sifter. A de-oiling device was a horizontally placed centrifugal machine, the dripping pills were separated from paraffin oil under the acceleration of 2000 G, Fufang Danshensu pills were obtained finally, the time taken by the above de-oiling process was not more than 30 seconds. Further Operations such as coating may be conducted next.

Employing the above-mentioned manufacturing method to formulate the production process may enable the capacity of the entire equipment to reach to 100 kg/h, with the material residue being less than 5 kg, and the time for materials passing through the equipment being less than 3 minutes; the feeding accuracy was controlled to be 0.5%, and the accuracy of dose can reach to 0.5‰.

Embodiment 2 Manufacture of Fufang Danshen Dripping Pills 600 g of extracts of Salvia Miltiorrhiza and Panax notoginseng, 5 g of borneol and 3000 g of PEG-6000 excipients were taken, after precise weighing was performed respectively, borneol and PEG-6000 were firstly heated for material combining, with the temperature being increased to 50° C.; then, they were further mixed with extracts of Salvia Miltiorrhiza and Panax notoginseng, and continuously heated to 55° C., the final temperature of the material mixture reaches to 70° C. after mixing, de-gassing, delivering and other steps were performed continuously, the time taken by the above material combining process was not more than 30 seconds. The homogenizing pressure was adjusted to be 1500 MPa to make the material mixture further be dispersed uniformly so as to reach to nano-scale dispersion, and the material temperature was further increased, the temperature of the material mixture at the outlet of the homogenizing device was 90° C., and the outlet pressure of the homogenizing device was 0.1 MPa. The material mixture was subjected to vibration dripping via a dripper, and the vibration frequency was adjusted to be 500 Hz, the material was dripped into a feed barrel containing liquid paraffin, the dripper was 1000 mm away from the top liquid level of the liquid paraffin, the height of the feed barrel was 10 m, the diameter of the feed barrel was 1000 mm, and the initial temperature of the inlet for the liquid paraffin was 0° C., a temperature gradient was formed from bottom to top in the feed barrel, which had a gradient range of 0-60° C., after the material was dripped into the liquid paraffin, under the action of temperature, the dripped material was cooled into solid dripping pills via sufficient cooling, and the dripped dripping pills had a diameter of 2 mm, wherein the time taken by the above dripping process was not more than 30 seconds. The de-oiling step was performed after the formed dripping pills were pre-filtrated together with the liquid paraffin via a sifter. A de-oiling device was a horizontally placed centrifugal machine, the dripping pills were separated from paraffin oil under the acceleration of 150 G, Fufang Danshensu pills were obtained finally, the time taken by the above de-oiling process was not more than 20 seconds. Further Operations such as coating may be conducted next.

Employing the above-mentioned manufacturing method to formulate the production process may enable the capacity of the entire equipment to reach to 120 kg/h, with the material residue being less than 5.5 kg, and the time for materials passing through the equipment being less than 2 minutes; the feeding accuracy was controlled to be 0.5%, and the accuracy of dose can reach to 0.6‰.

Embodiment 3 Manufacture of Huoxiang Zhengqi Dripping Pills 200 g of Huoxiang Zhengqi extract, 1 ml of patchouli oil, 2 ml of perilla oil and 40 g of polyethylene glycol were taken; after precise weighing was performed respectively, polyethylene glycol was firstly heated for material combining, with the temperature being increased to 45° C., then, it was further mixed with Huoxiang Zhengqi extract, patchouli oil and perilla oil, and continuously heated to 55° C., the final temperature of the material mixture reaches to 70° C. after mixing, de-gassing, delivering and other steps were performed continuously, the time taken by the above material combining process was not more than 60 seconds. The homogenizing pressure was adjusted to be 500 MPa to make the material mixture further be dispersed uniformly to reach to nano-scale dispersion, and the material temperature was further increased, the temperature of the material mixture at the outlet of the homogenizing device was 80° C., and the outlet pressure of the homogenizing device was 0.05 MPa. The material mixture was subjected to vibration dripping via a dripper, and the vibration frequency was adjusted to be 100 Hz, the material was dripped into a feed barrel containing liquid paraffin, the dripper was 700 mm away from the top liquid level of the liquid paraffin, the height of the feed barrel was 8 m, the diameter of the feed barrel was 100 mm, and the initial temperature of the inlet for the liquid paraffin was 5° C., a temperature gradient was formed from bottom to top in the feed barrel, which had a gradient range of 5-60° C., after the material was dripped into the liquid paraffin, under the action of temperature, the dripped material was cooled into solid dripping pills via sufficient cooling, and the dripped dripping pills had a diameter of 1 mm, the time taken by the above dripping process was not more than 50 seconds. The de-oiling step was performed after the formed dripping pills were pre-filtrated together with the liquid paraffin via a sifter. A de-oiling device was a horizontally placed centrifugal machine, the dripping pills were separated from paraffin oil under the acceleration of 500 G, Huoxiang Zhengqisu pills were obtained finally, the time taken by the above de-oiling process was not more than 25 seconds. Further operations such as coating may be conducted next.

Employing the above-mentioned manufacturing method to formulate the production process may enable the capacity of the entire equipment to reach to 95 kg/h, with the material residue being less than 4.5 kg, and the time for materials passing through the equipment being less than 3 minutes; the feeding accuracy was controlled to be 0.55%, and the accuracy of dose can reach to 0.5‰.

Embodiment 4 Manufacture of Andrographolide Dripping Pills 400 g of andrographolide, 800 g of PEG-6000 excipients and 800 g of PEG-4000 excipients were taken, after precise weighing was performed respectively, andrographolide, PEG-6000 and PEG-4000 were firstly heated for material combining, with the temperature being increased to 55° C., the final temperature of the material mixture reaches to 70° C. after mixing, de-gassing, delivering and other steps were performed continuously, the time taken by the above material combining process was not more than 45 seconds. The homogenizing pressure was adjusted to be 1500 MPa to make the material mixture further be dispersed uniformly to reach to nano-scale dispersion, and the material temperature was further increased, the temperature of the material mixture at the outlet of the homogenizing device was 90° C., and the outlet pressure of the homogenizing device was 5 MPa. The material mixture was subjected to vibration dripping via a dripper, and the vibration frequency was adjusted to be 300 Hz. The material was dripped into a feed barrel containing liquid paraffin, the dripper was 300 mm away from the top liquid level of the liquid paraffin, the height of the feed barrel was 1 m, the diameter of the feed barrel was 500 mm, and the initial temperature of the inlet for the liquid paraffin was 0° C., a temperature gradient was formed from bottom to top in the feed barrel, which had a gradient range of 0-60° C., after the material was dripped into the liquid paraffin, under the action of temperature, the dripped material was cooled into a solid dripping pill via sufficient cooling, and the dripped dripping pills had a diameter of 10 mm, the time taken by the above dripping process was not more than 55 seconds. The de-oiling step was performed after the formed dripping pills were pre-filtrated together with the liquid paraffin via a sifter. A de-oiling device was a horizontally placed centrifugal machine, the dripping pills were separated from paraffin oil under the acceleration of 500 andrographolide pills were obtained finally, the time taken by the above de-oiling process was not more than 25 seconds. Further operations such as coating may be conducted next.

Employing the above-mentioned manufacturing method to formulate the production process may enable the capacity of the entire equipment to reach to 110 kg/h, with the material residue being less than 5.2 kg, and the time for materials passing through the equipment being less than 2.5 minutes; the feeding accuracy was controlled to be 0.6%, and the accuracy of dose can reach to 0.55‰.

COMPARATIVE EXAMPLE

Traditional dripping of dripping pills: a pill dripping machine line disclosed by Chinese Patent ZL 200810153713.6 was employed to manufacture Fufang Danshen Dripping Pills.

It is illustrated below in the manner of lists that the present invention is superior to traditional manufacturing methods of dripping pills.

TABLE 1

Capacity Parameter Table for Various Embodiments and Comparative Example

| Case | Capacity | Particle Size of Dripping Pill | Manufacturing Time (for the manufacture of 10 KG of dripping pills) | Damage Rate of Products after De-oiling | De-oiling Time |
| --- | --- | --- | --- | --- | --- |
| Embodiment 1 | 1000-1250 pills/second | 0.2-4 mm | 6 min | Low | 30 s |
| Embodiment 2 | 1000-1250 pills/second | 2-4 mm | 6 min | Low | 25 s |
| Embodiment 3 | 1000-1250 pills/second | 2-4 mm | 6 min | Low | 28 s |
| Embodiment 4 | 1000-1250 pills/second | 2-4 mm | 6 min | Low | 27 s |
| Comparative Example | 1-2 pills/second | 2-4 mm | 30-45 min | High | 2 min |

As can be seen from the above embodiments and the comparative example, the present invention not only shortens the time required by the overall manufacturing process, ensures the dripping pills to be more stable, thus guaranteeing that the feeding accuracy and the accuracy of dose are stable. Furthermore, high-speed centrifugation was employed to de-oil dripping pills in a reasonable manner, preventing contamination of the dripping pills as well as improving the circulation utilization rate of cooling liquid.

The invention claimed is:

1. A method comprising
 1) weighing materials comprising a drug and excipients, wherein the relative standard deviation of the variation of the weight of the drug is less than or equal to 5%, and wherein the weight ratio of the drug to excipients is 1:5 to 5:1;
 2) transferring the materials to a homogenizing device comprising a mixing chamber and an outlet and mixing to obtain a material mixture;
 3) homogeneously applying 500-2000 MPa pressure and heating the material mixture to at least 50° C. for less than 30 seconds and to produce a homogenized material, and applying 0.1-5.0 MPa pressure to transfer the homogenized material through the outlet of the homogenizer device to a dripper;
 4) subjecting the dripper to vibrational frequency of 50-500 Hz to produce dripping pills and delivering the dripping pills into a cooling liquid within a barrel, wherein the cooling liquid has a temperature gradient of −15-60° C., from bottom to top of the barrel; and
 5) removing the cooling liquid on surfaces of the dripping pills by transferring the dripping pills to a sifter attached to a centrifuge, and centrifuging at 500-2000 G at an angle of 40-90 degrees for less than 20 seconds.

2. The method according to claim 1, wherein the cooling liquid has a temperature gradient with a range of −15-60° C., wherein the dripping pills pass through the cooling liquid from a first temperature to a second temperature, wherein the first temperature is greater than the second temperature.

3. The method according to claim 1, wherein the cooling liquid is paraffin, methylsilicone oil and/or kerosene.

4. The method according to claim 1, wherein the time taken by the dripping and cooling is not more than 60 seconds.

5. The method according to claim 1, wherein the drug is selected from one of extracts of Radix Bupleuri, *Salvia Miltiorrhiza*, Qishen, *Agastache* rugosus and Herba andrographitis and the extract of Fufang Danshen.

6. The method according to claim 5, wherein the excipient is selected from one or more of polyethylene glycol, sorbitol, xylitol, lactitol, maltose, starch, methylcellulose, carboxymethylcellulose, hydroxypropyl methylcellulose, Arabic gum, trehalose, dextrin, cyclodextrin, agar, and lactose.

7. The method according to claim 1, further performing a cycle comprising homogeneously applying pressure and increasing the temperature 0-10° C. to obtain a temperature of 55-65° C., and degassing the homogenized material and repeating the cycle twice to produce a homogenized material having a temperature of up to 80° C., wherein the three cycles are completed in less than 60 seconds.

8. The method according to claim 1, wherein the applied pressure is 500-1500 MPa.

9. The method according to claim 1, wherein the outlet pressure of the homogenizing device is 0.1-2.0 MPa.

10. The method according to claim 1, wherein the vibration frequency during dripping is 50-300 Hz.

11. The method according to claim 2, wherein the cooling liquid has a temperature gradient with a range of 0-60° C.; the initial temperature of the cooling liquid at the bottom of the feed barrel is 0-25° C.

* * * * *